(12) United States Patent
Melikyan et al.

(10) Patent No.: US 10,702,361 B2
(45) Date of Patent: Jul. 7, 2020

(54) METHOD AND DEVICE FOR THE VIBRATIONAL MECHANICAL ACTIVATION OF COMPOSITE MATERIALS

(71) Applicants: Melikset Litvinovich Melikyan, Glendale, CA (US); Karine Meliksetovna Melikyan, Glendale, CA (US)

(72) Inventors: Melikset Litvinovich Melikyan, Glendale, CA (US); Karine Meliksetovna Melikyan, Glendale, CA (US); Garegin Meliksetovich Melikyan, Moscow (RU)

( * ) Notice: Subject to any disclaimer, the term of this patent is extended or adjusted under 35 U.S.C. 154(b) by 0 days.

(21) Appl. No.: 15/082,140

(22) Filed: Mar. 28, 2016

(65) Prior Publication Data
US 2016/0206416 A1    Jul. 21, 2016

Related U.S. Application Data

(63) Continuation-in-part of application No. PCT/RU2014/000975, filed on Dec. 23, 2014.

(30) Foreign Application Priority Data

Oct. 23, 2013    (RU) ................................ 2013147270

(51) Int. Cl.
*A61C 13/15*    (2006.01)
*A61B 17/88*    (2006.01)
(Continued)

(52) U.S. Cl.
CPC ........ *A61C 19/003* (2013.01); *A61B 17/8833* (2013.01); *A61C 1/07* (2013.01); *A61C 3/03* (2013.01); *A61C 5/50* (2017.02)

(58) Field of Classification Search
CPC ........... A61C 19/003; A61C 5/04; A61C 1/07; A61C 5/50; A61C 3/03; A61M 37/0092
(Continued)

(56) References Cited

U.S. PATENT DOCUMENTS

| 150,943 | A | * | 5/1874 | Dennett | .................... | A61C 3/00 |
| | | | | | | 433/164 |
| 1,676,715 | A | * | 7/1928 | Snyder | ..................... | A61C 3/08 |
| | | | | | | 433/163 |

(Continued)

FOREIGN PATENT DOCUMENTS

| DE | 102007052442 | 5/2009 |
| RU | 2238696 | 10/2003 |

(Continued)

OTHER PUBLICATIONS

The criteria for assessing the quality . . . M. L. Melikyan, G. M. Melikyan and K. M. Melikyan // Institute of Dentistry. RU—Feb. 2011.—pp. 86-88.

(Continued)

*Primary Examiner* — Nicholas D Lucchesi

(57) ABSTRACT

The invention relates to medicine, namely to dentistry and is intended to reinforce composite materials used for elimination various defects of hard dental tissues of carious and non-carious origin in the process of direct/indirect, reinforced/unreinforced composite restoration. The claimed method includes vibrational mechanical activation of composite materials by a vibrational impact on portions of composite material shaped by manual mechanical activation (e.g., roll/ball) and applied layer by layer to a defect area. A device for vibrational mechanical activation of a composite material includes at least one working part for applying a composite material to a defect, the working part fixedly attached to a handle, which is connected by a framework to a micromotor that creates vibration which are transferred via (Continued)

the working portion to a layer of composite material by distributing the same across the entire surface of the defect and achieving the simultaneous surface plastic deformation thereof.

7 Claims, 1 Drawing Sheet

(51) Int. Cl.
*A61C 3/03* (2006.01)
*A61C 5/50* (2017.01)
*A61C 1/07* (2006.01)

(58) Field of Classification Search
USPC .................... 433/118, 119, 164, 215, 226
See application file for complete search history.

(56) References Cited

U.S. PATENT DOCUMENTS

| | | | | | |
|---|---|---|---|---|---|
| 2,696,048 | A | * | 12/1954 | Lindgren | A61C 3/08 433/162 |
| 3,890,713 | A | * | 6/1975 | Nielsen | B05C 17/00593 433/118 |
| 3,914,868 | A | * | 10/1975 | Schwartz | A61C 5/04 433/163 |
| 4,219,619 | A | | 8/1980 | Zarow | |
| 4,643,677 | A | * | 2/1987 | Kim | A61C 3/08 433/142 |
| 4,850,875 | A | | 7/1989 | Takatsu | |
| 5,151,030 | A | * | 9/1992 | Comeaux | A61C 1/07 433/118 |
| 5,244,933 | A | | 9/1993 | Eidenbenz et al. | |
| 5,639,238 | A | * | 6/1997 | Fishburne, Jr. | A61H 13/00 433/215 |
| 5,697,787 | A | * | 12/1997 | Schumacher | A61C 5/00 433/164 |
| 6,206,698 | B1 | * | 3/2001 | Billingsley | A61C 3/08 433/164 |
| 6,224,379 | B1 | * | 5/2001 | Abedian | A61C 3/08 433/224 |
| 7,014,462 | B1 | * | 3/2006 | Tilse | A61C 17/20 433/226 |
| 9,452,027 | B2 | * | 9/2016 | Kilcher | A61C 3/08 |
| 2002/0123703 | A1 | * | 9/2002 | Mark | A61C 3/08 601/46 |
| 2003/0186193 | A1 | * | 10/2003 | Comfort | A61C 3/08 433/147 |
| 2004/0038177 | A1 | * | 2/2004 | Rosen | A61C 3/06 433/142 |
| 2005/0026106 | A1 | * | 2/2005 | Jefferies | A61C 1/07 433/81 |
| 2005/0100860 | A1 | * | 5/2005 | Kameli | A61C 3/00 433/144 |
| 2007/0190485 | A1 | * | 8/2007 | Hayman | A61C 1/07 433/118 |
| 2008/0206706 | A1 | * | 8/2008 | Mossle | A61C 1/07 433/118 |
| 2008/0213731 | A1 | * | 9/2008 | Fishburne | A61C 3/00 433/217.1 |
| 2009/0130628 | A1 | * | 5/2009 | Viscomi | A61C 3/08 433/164 |
| 2009/0191505 | A1 | * | 7/2009 | Clark | A61C 5/04 433/39 |
| 2010/0233646 | A1 | * | 9/2010 | Brokx | A61C 5/062 433/36 |
| 2012/0000483 | A1 | * | 1/2012 | Snedden | A46B 9/005 132/321 |
| 2012/0237893 | A1 | * | 9/2012 | Bergheim | A61C 5/02 433/81 |
| 2013/0040267 | A1 | * | 2/2013 | Bergheim | A61C 5/02 433/216 |
| 2016/0128799 | A1 | * | 5/2016 | Lehtonen | A61C 3/00 433/141 |

FOREIGN PATENT DOCUMENTS

| | | |
|---|---|---|
| RU | 2004121429 | 1/2006 |
| RU | 2331385 | 2/2007 |
| RU | 2331386 | 8/2008 |
| RU | 2348374 | 3/2009 |
| RU | 2403886 | 11/2010 |
| RU | 2403887 | 11/2010 |
| RU | 2545410 | 3/2015 |
| SU | 164096 | 7/1964 |

OTHER PUBLICATIONS

Vestnik of the Dniepropetrovsk University, series "Physics. Radio electronics" 2007, issue 14, No. 12/ 1 Ukraine.
M. L. Melikyan (RDM) (Part I) by M. L. Melikyan, K. M. Melikyan, S. S. Gavriushin, K. S. Martirosyan, G. M. Melikyan // Institute of Dentistry.RU—Mar. 2012.—No. 56. p. 62-63.
Joseph Sabbagh "SonicFill system: a clinical approach" (Kerr News, May 2012, 10-13 pp., Switzerland).
"Composite, filling and facing materials". A.V. Borisenko and V.P. Nespryadko, Kiev, Kniga Plus, 2002 Ukraine.

* cited by examiner

METHOD AND DEVICE FOR THE VIBRATIONAL MECHANICAL ACTIVATION OF COMPOSITE MATERIALS

CROSS-REFERENCE TO RELATED APPLICATIONS

This application is a continuation-in-part of International Patent Application No. PCT/RU2014/000975, filed on Dec. 23, 2014, which claims priority to and the benefit of Russian Patent Application No. 2013147270, filed on Oct. 23, 2013, the entire disclosures of which are incorporated herein by reference.

FIELD

The invention relates to the field of dentistry and can be used to eliminate defects of dental hard tissues of the carious and noncarious origin, in the process of direct or indirect restorations with reinforced and unreinforced composites.

RELATED ART

Continuous development of adhesive technologies facilitated popularization of the usage of composite materials in dental practice. Currently, there are many chemical cure and light cure composite materials.

In clinical practice, light-cure composite materials are widely used to eliminate various defects of dental hard tissues.

The advantages of modem composite materials are that the composite materials have high physical and mechanical properties, biological inertness, excellent chemical resistance, low shrinkage factor, stronger adhesion and a better marginal adaptation to the hard tissues of the tooth.

Despite the obvious advantages, composite materials have a number of drawbacks typical to any artificial material used in dental practice.

There are many complications possible after elimination of defects of dental hard tissues by using composite materials. We distinguish complications that are eliminated in various ways:

Complications of I degree (mild)—the defect of the composite restoration is eliminated by polishing or by finishing and polishing;

Complications of II degree (medium)—the defect of the composite restoration is eliminated by a partial repeated composite restoration;

Complications of 111 degree (severe)—the defect of the composite restoration is eliminated by a total repeated composite restoration.

It is found that microsplits and macrosplits take place after the composite restoration. The methods of splits elimination are described in the article "The assessment criteria for of the restoration quality after the elimination of the coronal parts of anterior teeth using composite materials and metal mesh-contour reinforcing framework" by M. L. Melikyan, G. M. Melikyan and K. M. Melikyan//Institute of Dentistry—2011/2.—Pages 86—88.

A split is a partial destruction of the composite restoration.

Microsplits are insignificant defects of reinforced and unreinforced composite restorations, which are eliminated by finishing and polishing.

Macrosplits are partial defects of reinforced and unreinforced composite restorations, which are repaired with composite materials.

One of the main reasons for occurrence of splits of composite restorations is large (critical) defects of the type of voids. The nature of voids of the composite restorations has different nature.

In fact, presence of voids is an inherent property of any composite material as such. The voids ratio of composite materials depends on the following factors:

the quantitative ratio of the monomer and the filler;
the method of preparation of the material (when mixing the material, air bubbles are formed, causing porosity);
the damage of the pre-polymerized filler particles.

Among photopolymer materials, minimal porosity is characteristic of hybrid composites (0.18-2.5%), more porosity is characteristic of micro-filled materials (0.3-3.8%) and maximal porosity is characteristic of traditional materials (0.7-8.4%).

The voids ratio increases during restoration. The formation of pores with air bubbles is caused by the manipulations when applying of the composite material during the forming of the composite restoration. The formation of the restoration structure of the tooth consists of adhesion the composite material to the tooth structure and of adhesion fragments of the restorative material (layer by layer technique of restoration).

During air-oxygen free polymerization of the portions of the composite, the surface layer is polymerized and forms a strong bond between these portions of the composite. However, due to the interaction of the applied composite material layer surface with air oxygen, diffusing into the composite, an unpolymerized layer is formed, so-called "oxygen-inhibited layer" inhibited. The layer thickness is of 20-30 microns: The polymerization reaction is not possible in the layer, since the formation of the polymer matrix occurs only through the oxygen linkage, which are already linked by oxygen.

If there is an unpolymerized layer between the layers of the composite, then the portions of the composite do not bond to each other, so the connection surface becomes the place of mechanical weakness of the restoration and subsequent division into layers of the restoration under the mastication forces. The results of the spectrographic analysis of the sections of the composite materials confirmed the presence of voids of different nature, filled with air bubbles (see Vestnik of the Dnipropetrovsk University, series "Physics. Radio electronics", 2007, issue 14, No. 12/1).

The classification of voids and their descriptions are given in the article "Analysis of the strength properties of the mesh metalocomosite materials used in the reinforcement dentistry by M. L. Melikyan (RDM) (Part 1)" M. L. Melikyan, K. M. Melikyan, S. S. Gavriushin, K. S. Martirosyan, G. M. Melikyan//Institute of Dentistry.—2012/3. —No. 56—Pages 62-63.

The authors distinguish two types of microvoids present in within the composite restorations:

enclosed (internal);
dead-end (external).
Enclosed microvoids are located inside the restored tooth:
between the hard tissues of the tooth and the adhesive layer;
between the composite material and the adhesive layer;
within the portion of the composite material;
between the portions of the composite material.
Open blind microvoids are located on the external surface of the composite restoration.

According to the Griffith's theory, voids are not dangerous at low loads because they do not tend to increase. At high loads, they may be unstable, capable of rapid growth and coalescence with each other, formation of magistral cracks which lead to the composite restorations failure.

According to the mechanical principles, the destruction of the material does not occur simply under the load, but because the load causes a concentration of stress energy that is greater than that the material is capable to accumulate.

Considering that one of the main causes leading to the occurrence of splits of the composite restoration are large (critical) defects in the form of the voids, the development of technology that will reduce their number and size and, accordingly, will increase the strength of the composite restoration is an topical problem of dentistry. The solution to this problem will allow reducing the number of complications and increasing the lifespan of the composite restoration. The claimed invention is intended to solve this problem.

The solution to this problem, using the prior art methods, reduces to a certain sequence of making composite restorations. The following recommended steps of bonding portions of the composite are known:
  control of the presence of a superficial oxygen inhibited layer;
  placement of a portion of the composite material;
  control test of bonding;
  plastic processing of an applied portion of the composite material;
  control test;
  hardening of the form by directed polymerization;
  final polymerization of the portion of the composite material.

It is known from the literature that the main difficulties during the application of the first layer of the composite material to the floor cavity of the tooth are associated with stickiness of the composite to the plastic instrument and the formation of voids between the composite material and the adhesive layer.

Various solutions to this problem were suggested, but the problem still remains actual (J. Sabbagh. "SonicFill™ system: clinical approach". Dental Times—2012.—14.—Pages 6, 8).

To carry out the plastic processing of the applied portion of the composite material, the composite material is spread, with a plastic instrument, over the prepared surface of the tooth hard tissue that has been coated with an adhesive layer, or over the surface of the previously applied layer of the composite so that there are no air bubbles under it.

The whole surface of the applied portion of the composite is processed with a certain pressure using the plastic instrument, which ensures squeezing the oxygen-inhibited layer and adhesion the portion of the composite to the surface at a certain point, which is under pressure at this moment.

The method of reducing voids of the composite material, implemented in the known method, consists of "burnishing" the portion of the composite material by surface plastic deformation, using a sliding instrument, over the locally contacting it surface of the deformable material ("Composite, filling and facing materials". A. V. Borisenko and V. P. Nespryadko, Kiev, Kniga Plus, 2001). This method does not provide the maximal squeezing of air out form voids by a plastic instrument from the applied composite layer surface.

The disadvantage of this method is that usually during its implementation the redistribution of the voids, within the material is occurred due to their displacement by the smoothing mechanical action of the instrument. Therewith, the insignificant squeezing of air out of the voids is nonhomogeneous over the entire surface of the deformable material due to the absence of the equal controlled force impact of the plastic instrument upon the surface of the applied composite material.

To reduce voids and increase the strength of the composite material, the method of manual mechanical activation (MMA) of the composite material by M. L. Melikyan is currently used.

Mechanical activation of the composite material is a mechanical impact upon the composite material, which leads to an improvement of its physical and mechanical properties.

This method is described in the Russian Patents Nos. 2238696 and 2331385, the patent owners of which are M. L. Melikyan, G. M. Melikyan, K. M. Melikyan.

The essence of the invention according to Russian Patent No. 2238696 lies in that the missing coronal part is restored with the anatomic-topographical_and biomechanical features of the structure of the tooth, which is being restored, using a reinforced mesh-reinforced metalocomposite.

For the restoration of the missing enamel layer, the composite material is manually mechanical activated by fingers of the hands wearing powder-free textured latex gloves. Then, the shaped composite rolls are used to restore missing walls of the coronal part of the tooth.

The essence of the invention according to Russian Patent No. 2331385 is that during the elimination of the defect of the cutting edge up to the depth of 2 mm, the composite material is also manually activated during the composite roll formation.

The patent owners together with scientists from Bauman Moscow State Technical University investigated the influence of the method of manual mechanical activation (MMA) upon the strength properties of the composite material. The laboratory studies were conducted using the universal testing machine "Quasar 50" (Galdabini, Italy).

The tests were conducted using samples with the dimensions of length (1) 45 mm, height (a) and width (b) equal to 5 mm for static three-point bending test according to the pattern: "The concentrated load at midspan". During the tests, the diagram data on the load deformation—the maximum sag was read, as well as the failure load $F_{(N)}$ was determined.

To provide the static three-point bending test, series of the composite material specimens were made in total amount of 15 pieces (5 pieces in each series). All series of the specimens were made at room temperature and were kept in water after their manufacture before the test.

Series I (control series): the portions of the composite material (0.5 g) were measured out by squeezing the material out of a syringe, weighed, and without subjecting to any additional mechanical impact (mechanical activations) were placed into the mold. To produce specimens of series I using a plastic instrument, a portion of the composite material was extruded out of the syringe and 0.5 g was weighed, and then the portion was placed on the bottom of a polypropylene mold and evenly distributed over the bottom of the mold using L-shaped plastic instrument. Taking into account that the length of the specimen was 45 mm long, each composite layer was polymerized three times for 20 seconds along the length the polypropylene form, thus the polypropylene form was sequentially filled with the composite material layer by layer and polymerization was carried out.

The completed specimen was removed from the mold and control polymerization was carried out from the external surfaces. The weight of the specimen was measured using scales with the accuracy of ±0.01 g; the geometric dimensions of the specimen were measured with an electronic calliper with the accuracy of ±0.01 mm.

Series II: portions of the composite material (0.5 g) were measured by squeezing the material out of a syringe and weighed, and then using the method of manual mechanical impact (mechanical activation) formed into the shape of balls. The formed composite balls were put into the mold. To make specimen of series II using a plastic instrument, a portion of the composite material was squeezed out the syringe and 0.5 g was weighed. Then, the composite material (using method of mechanical activation) was formed into the shape of balls using the rotational movements of fingers in "Sempercare" textured powder-free latex examination gloves.

Next, the formed composite ball was placed on the bottom of the polypropylene form and, using the L-shaped plastic instrument, it was evenly distributed all over the bottom and polymerization was carried out.

Thus, layer by layer the polypropylene mold was filled with the composite material sequentially. The completed specimen was removed from the mold and the control polymerization was carried out from the external surfaces. Further, the weight and specified geometric dimensions of the samples were measured with the accuracy of ±0.01 mm. In the process of measuring, the arithmetic mean values of the specimen length, width and thickness were used.

Series III differed from series II in that the rolls were formed of the obtained balls (by using the method of mechanical activation). The formed composite rolls were placed into the mold. To make samples of series III using aplastic instrument, a portion of the composite material was squeezed out the syringe and 0.5 g of the composite material was weighed. Afterwards, using the rotational movements of the fingers in "Sempercare" diagnostic gloves, the composite material (using the method of mechanical activation) was formed into the shape of a ball, and then—into the shape of a roll. Next, the formed composite roll was placed on the bottom of the mold, and evenly distributed all over the bottom using the L-shaped plastic instrument and polymerization was carried out.

Thus, the polypropylene mold was filled with the composite material sequentially layer by layer. The completed specimen was removed from the mold and the control polymerization was carried out from the external surfaces. Further, the weight was measured and the specified geometric dimensions of the specimens were measured with the accuracy of ±0.01 mm. In the process of measuring, the arithmetic mean values of the specimens length, width and thickness were used.

Each specimen was assigned a serial number and arrows were used to indicate the direction of the load application.

Specimens of series I-III were tested for static three-point bending at the temperature of 20° C. The maximum force generated by the machine is 500 N.

The comparative results of testing strength characteristics by static three-point bending of the composite specimens of series I-III, depending on the testing method, are shown in Table 1.

TABLE 1

Comparative results of the fracture load for samples of series I-III made of micro-hybrid composite material

| Specimens | Series I | Series II | Series III |
|---|---|---|---|
| Methods of making specimens | Control specimens made without mechanical activation | Test specimens in the form of a composite ball made with mechanical activation | Test specimen in the form of a composite roll made with mechanical activation |
| Maximum load Fmax [N] | 168.58 | 178.28 | 180.92 |

The test results of the static three-point bending test of the composite specimens made of the microhybrid composite material revealed that during the formation of the composite material into the shape of a ball (using the method of mechanical activation) the maximum load of the specimen is increased by 5.7% in comparison with control specimens.

By formation the composite material into the shape of a roll (using the method of mechanical activation) the maximum load of the specimens increases by 7.3% in comparison with control specimens (without a roll).

The study has confirmed that the method of manual mechanical activation of the composite material decreases:
voids by 30%;
the maximum voids size (critical defects) by 45%;
the mean voids size by 3%.

The disadvantage of this method of manual mechanical activation lies in that shaping the composite material in the form of a roll in the course of the restoration is applied mainly during the restoration of missing walls of the crown part of the tooth, or during the repairing defects in the cutting edge of the tooth. That is, this method of mechanical activation is used to eliminate some specific defects.

The effect of increasing the strength of the composite restoration, achieved by using the known method, is not sufficient to obtain monolithic composite restoration (MCR).

SUMMARY

The claimed method of reducing voids and increasing the strength of the composite material is based on the use of a fundamentally new method of its hardening with vibrational mechanical activation (VMA).

During the defects elimination of dental hard tissues using the composite material by the claimed method, the layers of the composite material are subjected to vibrational impact (vibrational surface plastic deformation). In the process of implementation of the claimed method, each subsequent layer is subjected to vibrational impact prior to its polymerization.

Vibrational surface plastic deformation is a vibrational surface plastic deformation of the material due to mechanical vibration of the instrument (GOST 18296-72. The processing by surface plastic deformation. Terms and definitions).

The authors of the invention together with scientists of Bauman Moscow State Technical University conducted studies on the influence of the vibrational mechanical activation (VMA) impact of the composite material on the strength properties of this composite material using test methods described above.

Specimens of series I (control) made as described above, and specimens of series II, which differ from control specimens that during their manufacture each applied layer of the composite material was subjected to vibrational impact with the oscillation frequency of 1000 Hz before polymerization, were tested.

TABLE 2

Comparative results of the fracture load for specimens of series I-II made of micro hybrid composite material

| Specimen series | Series I | Series II |
|---|---|---|
| Methods of making specimens | Control specimen made without mechanical activation | Test specimen in the form of a composite roll made with mechanical activation |
| Maximum load $F_{max}$ [N] | 168.58 | 206.5 |

The test results the static three-point bending of the composite samples of series I and II revealed that the maximum, load of the specimens of series II, made of the microhybrid composite material, which was subjected to vibrational impact, increased by 22.5% in comparison with the control samples of series I.

As a result of the subsequent tests conducted together with scientists of Kazan Federal University (KFU), the dependence of the maximum load increases upon the voids ratio of the microhybrid composite material was established.

In comparison with the control specimens of series I, the specimens of series II subjected to vibrational mechanical activation feature:
  reduction of voids of the microhybrid composite material by 70%;
  reduction of the maximal voids size (critical defects) by 45%;
  reduction of the mean voids size by 3%.
In the specimens of series II, subjected to vibrational mechanical activation, the junction boundaries between the layers of the composite material are absent.

The advantages of the method of vibrational mechanical activation (VMA) of the composite material by M. L. Melikyan are:
  the maximum load increases by 22.5% (without installation of additional reinforcing elements into the composite material during the restoration);
  porosity decreases by 70%;
  the maximal voids size (critical defects) decreases by 45%;
  the mean voids size decreases by 3%.
The method of vibrational mechanical activation of the composite material is used:
  to eliminate any defects of dental hard tissues;
  for direct, indirect, reinforced and unreinforced composite restorations.
The method of vibrational mechanical activation of the composite material provides:
  the constant controlled force of the vibrational impact by the restoration instrument upon the portion of the composite material and its even distribution over the entire defect surface, which was subjected to adhesive processing, or upon the surface of the previously deposited and polymerized composite layer;
  the oriented direction of vibration impact inside the processed surface—perpendicular to the surface of the adhesive layer or the previous layer of polymerized composite material;
  effective air squeezing out of the voids (but not their redistribution from the surface of the previously deposited composite layer), and filling them with the composite material;
  significant size reduction of critical defects, which reduces the probability of appearance of splits of the composite restoration;
  tight and durable adhesion of the composite material to the adhesive layer and to each subsequent portion of the composite material;
  forming a solid condensed monolithic composite structure;
  effective marginal adaptation of the composite material to the hard tissues of the tooth, which helps reduce micro leakage and the formation of secondary caries.
The method of vibrational mechanical activation of the composite material decreases:
  the probability of complications and extends the lifespan of the composite restoration;
  retention of dyes by reducing the number and size of dead-open microvoids on the surface of the composite restoration, which ensures high aesthetics of the composite restoration;
  sorption of water and the formation of bacteria colonies;
  the probability of occurrence of voids between the adhesive layer and the composite material, and interlayer voids of the composite material due to the absence of the composite sticking to the instrument;
  the arm muscles tension, which occurs when the force from the hand is transmitted through the instrument to a portion of the composite material.
The application of the method of vibrational mechanical activation of the composite material allows:
  performing restoration without eye and finger strain, including tooth areas which can be difficult to access;
  reduce the composite restoration time due to the effective adhesion of the portion of the composite material to the adhesive or composite layer.

The method of vibrational mechanical activation of composite materials M. L. Melikyan is implemented as follows. During eliminating a defect of the coronal part of the tooth or during eliminating complications of the composite restoration (II and III degrees) known methods of layer by layer restoration/reconstruction of the coronal part of the tooth are applied using the composite materials, which methods have been described, including in the Russian patents for inventions, issued to patent owners M. L. Melikyan, G. M. Melikyan and K. M. Melikyan (Russian Patent No. 2273465, 2331386, 2403886, and 2403887). During implementation of the known layer by layer method of composite materials, each subsequent layer of the applied composite material is subjected to vibrational mechanical activation for 20 seconds with the vibration frequency of up to 1000 Hz before polymerization. The permissible level of vibration corresponds to the Sanitary Rule and Regulation (SanPiN), approved by Resolution No. 2 of the Goskomsanepidemnadzor State Committee for Sanitary Supervision and Disease Control of the Russian Federation on Jan. 19, 1996.

For the implementation of the claimed method, a special device for vibrational mechanical activation of the composite material is used.

BRIEF DESCRIPTION OF THE DRAWINGS

A better understanding of this invention will be had by now referring to the accompanying drawing in which.

DETAILED DESCRIPTION

Figure 1:
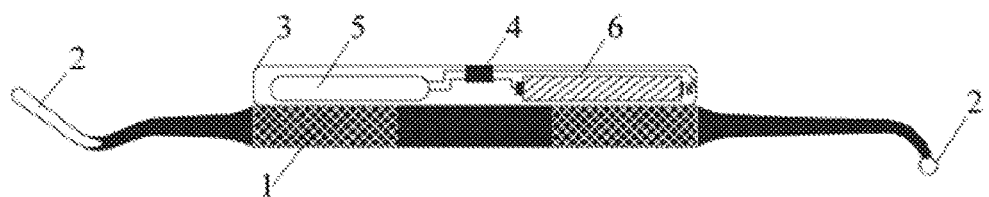
FIG. 1 is a view of a first embodiment of the special device for vibrational mechanical activation of the composite material in accordance with the present invention.
Figure 2:
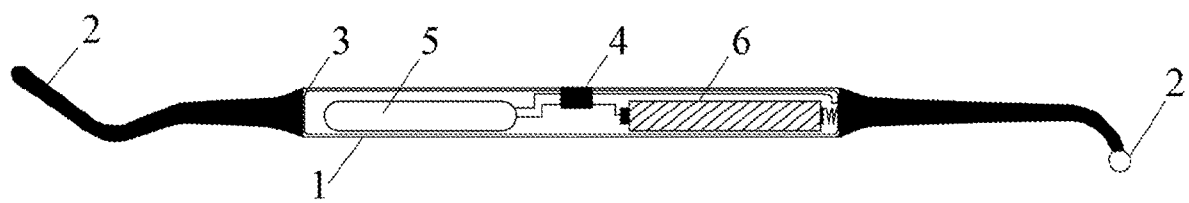
FIG. 2 is a view of second embodiment of the special device for vibrational mechanical activation of the composite material in accordance with the present invention.

The device (FIG. 1 and FIG. 2) illustrated in FIGS. 1 and 2 includes a handle 1, for example, in the form of a tubular body, at one end or at both ends of which one or two working elements 2 are fixedly attached and used for applying a portion of the composite material to the defect area of the coronal part of the tooth and its distribution over the defect surface using vibrational impact. The design of the device and the working elements 2 is similar to the plastic instrument. As illustrated in the figures, the plastic instrument in double-ended, with a first working element 2 in shape of a ball and an opposite second working element 2 in a shape of a paddle.

The handle 1 includes a fixing device—a removable framework 3 for fixation the battery power supply 6 and a micromotor 5, which is connected to the power supply 6 and generates vibration. There is a button 4 of the actuating element placed on the handle 1 for switching the power supply 6 on/off by pressing the button 4.

The embodiments of the device provide for placing the power supply 6 and the micromotor 5 outside the handle (FIG. 1) or inside the tubular body of the handle 1 (FIG. 2).

In the embodiment of FIG. 1, to fix the power supply 6 and the micromotor 5 outside the tubular body, the removable framework 3 with finger grips is used as the fixing device. The battery power supply 6 and the micromotor 5 are fixed internally to the framework 3.

In the embodiment of FIG. 2 with the location of the framework 3 inside the tubular body of handle 1, a window may be provided in the inner wall of the tubular body, for the internal placement of the battery power supply 6 and of the micromotor 5. The framework 3 is fixed in an opening to the window by interference fit.

In cases of the internal and external placement of the removable framework 3, the framework 3 serves as a cover that insulates the battery power supply 6 and the micromotor 5 from the external environment. In case the battery power supply 6 should be replaced, the framework 3 is taken off or out, the spent battery is removed and replaced with a new one.

The device for vibrational mechanical activation of the composite material operates as follows.

A portion of the composite material is applied, using the working element 2, to the surface in the area of the defect of the coronal part of the tooth.

Using button 4 of the actuating element, the power supply 6 is switched on and electrically connected to the micromotor 5. The activated micro-motor 5 generates vibrations that are transmitted to the working element 2, whereby vibrational mechanical activation of the deposited layer of the composite material is performed. The composite material is distributed under the impact of this vibration over the entire surface of the defect and is simultaneously subjected to surface plastic deformation for no less than 20 seconds. Then, using button 4 the actuating element, the power supply 6 is switched off. The device returns to the static condition and is ready for the application of the next portion of the composite material.

After the vibrational impact has been completed, the layer of the composite material that has been subjected to the vibrational mechanical activation is polymerized in a conventional manner.

Then, a new portion of the composite material is applied, which is subjected to vibrational mechanical activation in accordance with the procedure described above. The operations of applying portions of the composite material, the vibrational impact and polymerization are repeated until the full restoration of the integrity of the hard tissues of the tooth.

While the invention has been particularly shown and described as referenced to the embodiments thereof, those skilled in the art will understand that the foregoing and other changes in form and detail may be therein without departing from the spirit and scope of the invention.

The invention claimed is:

1. A method of vibrational mechanical activation of a composite material in direct or indirect, reinforced or unreinforced layer by layer composite restoration of a tooth, the method comprising
   manually mechanically activating a portion of a composite material to obtain a shaped portion of a composite material,
   applying the shaped portion of a composite material as an applied layer to a defect area or upon a surface of a previously applied and polymerized composite layer,
   after the applying, subjecting the applied layer of a composite material to a vibrational impact, polymerizing the applied layer of a composite material,
   wherein said applying is repeated for a further shaped portion of a composite material and said subjecting to a vibrational impact and said polymerizing are repeated for each subsequent applied layer until the full restoration of the tooth is achieved.

2. The method according to claim 1, wherein the vibrational impact on the shaped portions of composite material is performed with an oscillation frequency up to 1000 Hz.

3. The method according to claim 1, wherein the manually mechanical activated shaped portions of composite material are subjected to the vibrational impact for no less than 20 seconds.

4. The method of claim 1, wherein a portion of a composite material is mechanically activated into a ball-shape portion or a roll-shaped portion.

5. A device for vibrational mechanical activation of a composite material in direct or indirect layer by layer composite restoration, the device comprising at least one working part for applying the composite material to a defect area of a tooth or upon a surface of a previously applied and polymerized composite layer, wherein the at least one working part is fixedly attached to a handle, wherein the handle is formed as a tubular body provided with a button of an activating element for actuating a battery power supply, electrically connected to a micromotor, generating vibrations, which through the at least one working part are transmitted to a layer of the composite material through its distribution over the entire surface of a defect of the tooth or upon the surface of the previously applied and polymerized layer and simultaneous surface plastic deformation,
   wherein the battery power supply and the micromotor are placed in a framework, removably attachable to the tubular body by a fixing appliance in an opening of a window made on a lateral surface of the tubular body.

6. The device according to claim 5, wherein the device comprises two working parts attached to the handle at the opposing ends thereof, respectively.

7. The device according to claim 6, wherein one of the working parts has a shape of a ball and the other working part has a shape of a paddle.

\* \* \* \* \*